(12) United States Patent
Parker et al.

(10) Patent No.: US 7,045,296 B2
(45) Date of Patent: May 16, 2006

(54) PROCESS FOR ANALYZING PROTEIN SAMPLES

(75) Inventors: Kenneth C. Parker, Hopkinton, MA (US); Timothy K. Nadler, Framingham, MA (US); George J. Vella, Medway, MA (US); Yulin Huang, Westwood, MA (US); Rudolf H. Aebersold, Mercer Island, WA (US); Marcus B. Smolka, Sao Paulo (BR)

(73) Assignees: Applera Corporation, Framingham, MA (US); Institute for Systems Biology, Seattle, WA (US)

( * ) Notice: Subject to any disclaimer, the term of this patent is extended or adjusted under 35 U.S.C. 154(b) by 515 days.

(21) Appl. No.: 09/851,058

(22) Filed: May 8, 2001

(65) Prior Publication Data

US 2002/0192720 A1 Dec. 19, 2002

(51) Int. Cl.
*G01N 33/53* (2006.01)
*G01N 24/00* (2006.01)

(52) U.S. Cl. .......................... 435/7.1; 435/4; 435/7.92; 435/24; 435/177; 435/188; 435/964; 436/173; 436/175; 436/165; 436/168

(58) Field of Classification Search ............... 435/4, 435/7.1, 7.92, 24, 177, 188, 964, 5, 6, 7.5, 435/15, 21, 68.1, 97; 436/173, 175, 165, 436/168, 87, 89, 94; 530/334–337, 402, 412, 530/417

See application file for complete search history.

(56) References Cited

U.S. PATENT DOCUMENTS

| | | | | |
|---|---|---|---|---|
| 5,538,897 | A | * 7/1996 | Yates, III et al. | ............. 436/89 |
| 6,017,693 | A | * 1/2000 | Yates, III et al. | ............... 435/5 |
| 6,043,025 | A | 3/2000 | Minden et al. | ................. 435/4 |
| 6,127,134 | A | 10/2000 | Minden et al. | ............. 435/7.2 |

FOREIGN PATENT DOCUMENTS

WO    WO 00/11208    * 3/2000

OTHER PUBLICATIONS

Sechi et al., "Modification of cysteine residues by alkylation. A tool in peptide mapping and protein identification." Analytical Chemistry. 1998, vol. 70, pp. 5150–5158.*

Bienvenut et al., "Toward a clinical molecular scanner for proteome research: parallel protein chemical processing befor and during Western Blot." Analytical Chemistry, 1999, vol. 71, pp. 4800–4807.*

Clauser et al., "Rapid mass spectrometric peptide sequencing and mass matching for characterization of human melanoma proteins isolated by two–dimensional PAGE." Proceeding of the National Academy of Science, USA, vol. 92, pp. 5072–5076, 1995.*

Gygi et al., "Quantitative analysis of complex protein mixtures using isotope–coded affinity tags." Nature Biotechnolgy, vol. 17, 1999, pp. 994–999.*

Conrads et al., "Utility if accurate mass tags for proteome–wide protein identification." Analytical Chemistry, 2000, vol. 72, pp. 3349–3354.*

Opitek et al., Comprehensive On–Line LC/LC/MS of Proteins. Analytical Chemistry 1997 69:1518–1524.

Ducret et al, High Throughput Protein Characterization by Automated Reverse–Phase Chromatagraphy/Electrospray Tandem Mass Spectrometry. Protein Science 1998 7:706–719.

Sechi et al, Modification of Cysteine Residues by Alkylation. A Tool in Peptide Mapping and Protein. Identification Analytical Chemistry 1998 70:5150–5158.

Gygi et al, "Quantitative Analysis of Complex Protein Mixtures Using Isotope–Coded Affinity Tags." Nature Biotechnology 1999 17: 994–999.

Link et al, Direct Analysis of Protein Complexes Using Mass Spectrometry. Nature Biotechnology 1999 17: 676–682.

Bienvenut et al, Toward A Clinical Molecular Scanner for Proteome Research: Parallel Protein Chemical Processing Before and During Western Blot. Analytical Chemistry 1999 71: 4800–4807.

(Continued)

*Primary Examiner*—Long V. Le
*Assistant Examiner*—Lisa V. Cook
(74) *Attorney, Agent, or Firm*—Andrew T. Karnakis

(57) ABSTRACT

Methods using gel electrophoresis and mass spectrometry for the rapid, quantitative analysis of proteins or protein function in mixtures of proteins derived from two or more samples in one unit operation are disclosed. In one embodiment the method includes (a) preparing an extract of proteins from each of at least two different samples; (b) providing a set of substantially chemically identical and differentially isotopically labeled protein reagents; (c) reacting the extract of proteins from different samples of step (a) with a different isotopically labeled reagent from the set of step (b) to provide two or more sets of isotopically differentially labeled proteins; (d) mixing each of the two or more sets of isotopically labeled proteins to form a single mixture of isotopically differentially labeled proteins; (e) electrophoresing the mixture of step (d) by an electrophoresing method capable of separating proteins within the mixture; (f) digesting at least a portion of one or more separated proteins of step (e) and (g) detecting the difference in the expression levels of the proteins in the two samples by mass spectrometry based on one or more peptides in the sample of labeled peptides. The analytical method can be used for qualitative and particularly for quantitative analysis of global protein expression profiles in cells and tissues, i.e. the quantitative analysis of proteomes.

22 Claims, 3 Drawing Sheets

OTHER PUBLICATIONS

Gygi et al, Evaluation of Two–Dimensional Gel Electrophoresis–Based Proteome Analysis Technology. Proceedings of the National Academy of Sciences 2000 97: 9390–9395.

Chen et al, Site–Specific Mass Tagging with Stable Isotopes in Proteins for Accurate and Efficent Protein Indentification. Analytical Chemistry 2000 72: 1134–1143.

Unlu et al, Difference Gel Electorphoresis: A Single Gel Method for Detecting Changes in Protein Extracts. Electrophoresis 1997 18: 2071–2077.

Unlu et al, Proteomics. Biochemical Society Transactions 27, Part 4 (Apr. 7–9 1999 University of Glasgow) of Techniques Group/Protein and Peptide Science Group/British Electrophoresis Society Joint Colloquium.

Yates et al, Direct Analysis of Proteins in Mixtures. Methods in Molecular Biology 2000 146: 17–26.

* cited by examiner

PROCESS FOR ANALYZING PROTEIN SAMPLES

FIELD OF THE INVENTION

This invention relates to a process for detecting differences in protein composition between complex protein samples such as cell lysates, cell extracts, or tissue extracts. More particularly this invention relates to a process for analyzing protein compositions using gel electrophoresis utilizing at least two labeled reagents capable of detecting such differences.

BACKGROUND OF THE INVENTION

Two dimensional (2D) electrophoresis has long been a mainstay in the quantitative analysis of complex mixtures of proteins, as from cell lysates or organelles. The traditional approach for quantifying proteins is to perform image analysis of the gels. The proteins can be detected by staining the proteins, by autoradiography, or even by using antibodies specific for certain proteins (Western blotting). Although powerful software has been developed to quantify the amount of protein that migrates to a spot in a gel, there is a limit to how much information can be obtained by such analyses even if the gels are perfectly reproducible and even if the software for spot analysis is able to resolve ambiguities of overlapping spots and uneven backgrounds. Recently, mass spectrometric techniques were described in published PCT International Application WO 00/11208 in which stable isotopes are incorporated into peptides derived from each proteins that bypasses the need for gels and for image analysis of any kind, because quantitation is performed by a mass spectrometer. However, when proteins are digested ahead of time, almost all information relating to protein chemical modification is lost, and the quantitative information for different proteins that share the peptide that is detected is combined together.

Proteins are essential for the control and execution of virtually every biological process. The rate of synthesis and the half-life of proteins and thus their expression level are also controlled post-transcriptionally. Furthermore, the activity of proteins is frequently modulated by post-translational modifications, in particular protein phosphorylation, and dependent on the association of the protein with other molecules including DNA and proteins. Neither the level of expression nor the state of activity of proteins is therefore directly apparent from the gene sequence or even the expression level of the corresponding mRNA transcript. It is therefore highly desirable that a complete description of a biological system include measurements that indicate the identity, quantity and the state of activity of the proteins which constitute the system. The large-scale (ultimately global) analysis of proteins expressed in a cell or tissue has been termed proteome analysis. Proteome analysis permits the detection and monitoring of differences in cell structure, function and development. The capability of determining differences in protein content between normal cells and abnormal cells such as cancerous cells is a valuable diagnostic tool.

At present no protein analytical technology approaches the throughput and level of automation of presently available genomic technology. The most common implementation of proteome analysis is based on the separation of complex protein samples most commonly by 2D gel electrophoresis (2DE) and the subsequent sequential identification of the separated protein species, typically by mass spectrometry. This approach has been revolutionized by the development of powerful mass spectrometric techniques and the development of computer algorithms which correlate protein and peptide mass spectral data with sequence databases and thus rapidly and conclusively identify proteins. This technology has reached a level of sensitivity which now permits the identification of essentially any protein which is detectable by conventional protein staining methods including silver staining. In the 2 DE/MS$^n$ method, proteins are quantified by densitometry of stained spots in the 2DE gels, followed by mass spectrometry (MS), tandem mass spectrometry (MSMS or MS$^2$), or multiple rounds of mass spectrometry (MS)$^n$. Alternatively, the staining step can be omitted, and the proteins can be detected by mass spectrometry, for example, by analyzing extracts of every slice from a 1D gel, or from every piece of a 2D gel, or by scanning membranes onto which digests from such gels have been deposited by transblotting (Bienvenut et al., Anal. Chem. 71:4800–4807, 1999).

In gel electrophoresis, proteins can be separated into individual components according to differences in mass by electrophoresing a protein mixture in a polyacrylamide gel under denaturing conditions. One dimensional and two dimensional gel electrophoresis have become standard tools for studying proteins. One dimensional SDS (sodium dodecyl sulfate) electrophoresis through a cylindrical or slab gel reveals only the major proteins present in a sample tested. Two dimensional polyacrylamide gel electrophoresis (2D PAGE), which separates proteins by isoelectric focusing, i.e., by charge, in one dimension and by size in the second dimension, provides higher resolving power, which is important when there are many proteins in the sample. The proteins migrate in one-or two-dimensional gels as bands or spots respectively. The separated proteins are visualized by a variety of methods, such as by staining with a protein specific dye, by protein mediated silver precipitation, autoradiographic detection of radioactively labeled protein, and by covalent or non-covalent attachment of fluorescent compounds. Immediately following the electrophoresis, the resulting gel patterns may be visualized by eye, photographically or by electronic image capture, for example, by using a cooled charge-coupled device (CCD). To compare samples of proteins from different cells or different stages of cell development by conventional methods, each different sample is presently run on separate lanes of a one dimensional gel or separate two dimensional gels. Comparison is by visual examination or electronic imaging, for example, by computer-aided image analysis of digitized one or two dimensional gels. The goal of such research is often to determine which proteins out of the hundreds of proteins that can be detected have changed in expression level between a control sample and one or more experimental samples.

Two dimensional gel electrophoresis has been a powerful tool for resolving complex mixtures of proteins. The differences in migration between the proteins, however, can be subtle. Imperfections in the gel can interfere with accurate observations. In order to minimize the imperfections, the gels provided in commercially available electrophoresis systems are prepared with exacting precision. Even with meticulous controls, no two gels are identical. The gels may differ one from the other in pH gradients or uniformity. In addition, the electrophoresis conditions from one run to the next may be different. Computer software has been developed for automated alignment of different gels. However, all of the software packages are based on linear expansion or contraction of one or both of the dimensions on two dimensional gels. The software has difficulty adjusting for local distortions in the gels. The ideal way to overcome such limitations is to combine the two samples prior to gel electrophoresis, assuming the two samples can be distinguished from one another at the analysis stage.

It has been proposed in U.S. Pat. Nos. 6,043,025 and 6,127,134 to provide a process for analyzing protein compositions from at least two samples wherein one sample is stained with a first dye and a second sample is stained with a second dye. The samples then are separated either by a 1D or 2D gel electrophoresis process to effect protein separation into a plurality of spots. A spot of interest then is analyzed to determine the difference in luminescent intensity of the dyes thereby to determine protein concentration from each sample. The camera is able to distinguish between the two dyes by the wavelengths of the emitted light, although dynamic range can be compromised due to a small amount of spectral overlap between the dyes. For this quantitation to be precise, the two species of proteins must migrate to exactly the same spot, ideally the same position as the unmodified protein. In some instances, only a small proportion of the protein is initially stained with the dyes. If there is any separation of stained from unstained proteins, then some fluorescent proteins may co-migrate with unrelated unstained proteins, resulting in misleading identifications in cases in which the protein is identified post electrophoresis.

The development of methods and instrumentation for automated, data-dependent electrospray ionization (ESI) tandem mass spectrometry ($MS^n$) in conjunction with microcapillary liquid chromatography (μLC) and database searching has significantly increased the sensitivity and speed of the identification of gel-separated proteins. As an alternative to the 2DE/$MS^n$ approach to proteome analysis, the direct analysis by tandem mass spectrometry of peptide mixtures generated by the digestion of complex protein mixtures has been proposed (Ducret et al., Prot. Sci. 7:706–719,1998). Tandem μLC/MSMS has also been used successfully for the large-scale identification of individual proteins directly from mixtures without gel electrophoretic separation (Yates et al., Methods Mol. Biol., 146: 17–26, 2000; Link et al., Nat. Biotechnol. 17:676–82, 1999; Opitek et al., Anal. Chem. 64: 1518–1524, 1997). While these approaches dramatically accelerate protein identification, the absolute or relative quantities of the analyzed proteins cannot be easily determined, and these methods have not been shown to substantially alleviate the dynamic range problem also encountered by the 2 DE/MSMS approach (Gygi et al., Proc. Natl. Acad. Sci. USA 17:9390–5, 2000). Therefore, low abundance proteins in complex samples are also difficult to analyze by the μLC/MSMS method without their prior enrichment.

An alternative to quantifying proteins in complex mixtures after SDS PAGE or 2D PAGE on the basis of staining intensity using conventional protein stains or fluorescent stains is to use protein stains to localize the regions of interest. Following proteolytic digestion, the peptides may then be labeled with stable isotopes, for example with deuterated nicotinoyloxysuccinimide (Munchbach, Quadroni, Miotto and James, Anal. Chem. A, 2000), which allows mass spectrometry to be used for quantitation. This approach suffers from the drawback that the protein ratio obtained is dependent on how carefully the spots are excised from the gel. Also, the control and the experimental sample must be run on separate gels.

Alternatively, isotopically labeled amino acid precursors may be introduced specifically into one of the two samples prior to proteolytic digestion (Sechi and Chait, Anal. Chem., 24:5150–8, 1998, Chen, Smith and Bradbury, Anal. Chem. 72: 1134–1143, 2000). This approach suffers from the drawback that the proteins must be isolated from culture conditions that allow close to complete replacement of the unlabeled amino acid precursors by the labeled precursors, or the intensity of each peptide will be spread out over a larger isotope cluster than usual, compromising both sensitivity and quantitation.

Recently, an approach was developed involving isotope coded affinity tags (ICAT™) that combines the incorporation of stable isotopes into the cysteine-containing peptides of proteins with the ability to affinity purify these modified peptides and to subsequently detect the proteins by mass spectrometry (Gygi et al., Nat Biotechnol., 17:994–9, 1999). Reagents useful in carrying out this method are commercially available from Applied Biosystems (Foster City, Calif.) under the ICAT™ brand. Because proteins typically have a small number of cysteine residues, it becomes possible to identify large numbers of proteins by focusing on a small subset of the peptides that are generated upon proteolytic digestion, making it possible to penetrate further into the proteome without being overwhelmed by large numbers of peptides from the most abundant proteins. Because the quantitation is performed by mass spectrometry, two or more samples can be combined together prior to analysis, so that artifactual sample processing differences do not affect the results so long as they take place after cysteine modification.

There are, however, several limitations to the previously described ICAT reagent based technology that in certain cases limit the information that can be obtained from the experiment. The cysteine containing peptides should be sufficiently long to uniquely identify proteins (or classes of homologous proteins). Because each peptide is separately purified, $MS^n$ techniques are often used to identify the protein from which the peptide was derived, instead of the simpler peptide mass fingerprinting (PMF) technique. No information is retained about the intact molecular weight of the protein(s) from which the cysteine-containing peptide was derived, or whether the protein was chemically modified by phosphorylation. Finally, no information is obtained from proteins that do not contain cysteine.

The present invention combines mass spectrometric quantitation with the resolving power of 2D electrophoresis so that differences in protein compositions from two or more samples containing complex mixtures can be determined from a single 2D gel. This extension to the current state of ICAT reagent technology overcomes each of the foregoing limitations. Proteins are modified by using the same ICAT reagent technology as before. However, all the advantages of protein separation by 2D gels are preserved. Although analysis of the ICAT reagent labeled peptides themselves usually leads to no information about the chemical modification of the protein from which they derived, the position of the protein on the gel is indicative of whether the protein was modified. Also, the chemically modified peptides themselves are present in the same spot, thus the ICAT reagent labeled peptides can still be used for quantitation of the relative amounts of each of the modified species. In addition, ICAT reagent containing peptides of any length are now informative because any one spot contains very few proteins. This also makes it possible to use PMF to identify the proteins, including any non-cysteine containing proteins that may be present at the same spot on the gel. These techniques still allow simultaneous processing of two or more samples such as those obtained from an experimental and a control sample. This same combination of technologies is also applicable to less resolving gel systems like 1D SDS PAGE gel analysis, 1D isoelectric focusing gels and the like.

SUMMARY OF THE INVENTION

This invention provides methods based upon 1D and 2D gel electrophoresis and mass spectrometry for the rapid, quantitative analysis of proteins or protein function in mixtures of proteins derived from two or more samples in one unit operation. Thus, only one gel must be performed in order to deduce which proteins have changed in expression level between the experimental sample and the control sample because the quantitation is determined by mass spectrometry. The analytical method can be used for qualitative and particularly for quantitative analysis of global protein expression profiles in cells and tissues, i.e. the quantitative analysis of proteomes. The method can also be employed to screen for and identify proteins whose expression level in cells, tissue or biological fluids is affected by a stimulus (e.g., administration of a drug or contact with a potentially toxic material), by a change in environment (e.g., nutrient level, temperature, passage of time) or by a change in condition or cell state (e.g., disease state, malignancy, site-directed mutation, gene knockouts) of the cell, tissue or organism from which the sample originated. The proteins identified in such a screen can function as markers for the changed state. For example, comparisons of protein expression profiles of normal and malignant cells can result in the identification of proteins whose presence or absence is characteristic and diagnostic of the malignancy.

The methods herein can also be used to implement a variety of clinical and diagnostic analyses to detect the presence, absence, deficiency or excess of a given protein or protein function in a biological fluid (e.g., blood), or in cells or tissue. The method is particularly useful in the analysis of complex mixtures of proteins, i.e., those containing 5 or more distinct proteins or protein functions. This method can also be used to look for absolute, quantitative changes if specific calibrated standards are labeled.

As with the techniques described in the aforementioned published PCT patent application (WO 00/11208), the present invention employs an isotopically labeled protein which can be either an affinity-labeled protein reactive reagent or non-affinity labeled protein reactive reagent that allows for the selective isolation of peptide fragments from complex mixtures. First, the control and the experimental sample(s) are labeled separately with different isotopic variants of the ICAT reagent, and are then combined. Separation of the protein components of the two or more samples is effected by either 1D or 2D gel electrophoresis followed by protein digestion. The isolated peptide fragments or reaction products are characteristic of the presence of a protein in those mixtures. Isolated peptides are characterized by mass spectrometric (MS) techniques. The most abundant proteins may be identified by peptide mass fingerprinting. Alternatively, the sequence of isolated peptides can be determined using tandem MS ($MS^n$) techniques, and by application of presently available sequence database searching techniques, the protein from which the sequenced peptide originated can be identified. The reagents utilized in the process of this invention provide for differential isotopic labeling of the isolated peptides that facilitates quantitative determination by mass spectrometry of the relative amounts of proteins in different samples. Also, the use of differentially isotopically labeled reagents as internal standards of known concentration facilitates quantitative determination of the absolute amounts of one or more proteins or reaction products present in the sample.

In general, the affinity labeled protein reactive reagents utilized in the process of this invention have three portions: an affinity label (A) covalently linked to a protein reactive group (PRG) through a linker group (L):

A-L-PRG

The linker may be differentially isotopically labeled, e.g., by substitution of one or more atoms in the linker with a stable isotope thereof. For example, hydrogen atoms can be substituted with deuterium atoms or $^{12}C$ with $^{13}C$.

The non-affinity labeled protein reactive reagents utilized in the process of this invention have two portions: a protein reactive group (PRG) and a linker group (L):

L-PRG which are as defined above.

The affinity label A functions as a molecular handle that selectively binds covalently or non-covalently, to a capture reagent (CR). Binding to CR facilitates isolation of peptides labeled with A. In specific embodiments, A is a streptavidin or avidin. After affinity isolation of affinity tagged materials, some of which may be isotopically labeled, the interaction between A and the capture reagent is disrupted or broken to allow MS analysis of the isolated materials. The affinity label, when utilized, can be displaced from the capture reagent by addition of displacing ligand, which may be free A or a derivative of A, or by changing solvent (e.g., solvent type or pH) or temperature conditions or the linker may be cleaved chemically, enzymatically, thermally or photochemically to release the isolated materials for MS analysis.

The type of PRG group that is specifically provided herein include those groups that selectively react with a protein functional group to form a covalent or non-covalent bond tagging the protein at specific sites. In specific embodiments, PRG is a group having specific reactivity for certain protein groups, such as specificity for sulfhydryl groups, and is useful in general for selectively tagging proteins in complex mixtures. A sulfhydryl specific reagent tags proteins containing cysteine.

Exemplary reagents useful in the process of this invention have the general formula

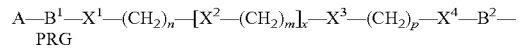

where:

A is optionally present and is the affinity label;

PRG is the protein reactive group;

$X^{1'}$, $X^2$, $X^3$ and $X^4$, independently of one another, and $X^2$ independently of other $X^2$ in the linker group, can be selected from O, S, NH, NR, $NRR'^+$, CO, COO, COS, S—S, SO, $SO_2$, CO—NR', CS—NR', Si—O, aryl or diaryl groups or $X^1$-$X^4$ may be absent, but preferably at least one of $X^1$-$X^4$ is present;

$B^1$ and $B^2$, independently of one another, are optional moieties that can facilitate bonding of the A or PRG group to the linker or prevent undesired cleavage of those groups from the linker and can be selected, for example, from COO, CO, CO—NR', CS—NR' and may contain one or more $CH_2$ groups alone or in combination with other groups, e.g.$(CH_2)_q$—CONR', $(CH_2)_q$—CS—NR', or $(CH_2)_q$;

n, m, p and q are whole numbers that can have values from 0 to about 100, preferably one of n, m, p or q is not 0 and x is also a whole number that can range from 0 to about 100 where the sum of n+xm+p+q is preferably less than about 100 and more preferably less than about 20;

R is an alkyl, alkenyl, alkynyl, alkoxy or aryl group; and
R' is a hydrogen, an alkyl, alkenyl, alkynyl, alkoxy or aryl group.

One or more of the $CH_2$ groups of the linker can be optionally substituted with small ($C_1$–$C_6$) alkyl, alkenyl, or alkoxy groups, an aryl group or can be substituted with functional groups that promote ionization, such as acidic or basic groups or groups carrying permanent positive or negative charge. One or more single bonds connecting $CH_2$ groups in the linker can be replaced with a double or a triple bond. Preferred R and R' alkyl, alkenyl, alkynyl or alkoxy groups are small having 1 to about 6 carbon atoms.

One or more of the atoms in the linker can be substituted with a stable isotope to generate one or more substantially chemically identical, but isotopically distinguishable reagents. For example, one or more hydrogens in the linker can be substituted with deuterium to generate isotopically heavy reagents.

In an exemplary embodiment the linker contains groups that can be cleaved to remove the affinity tag. If a cleavable linker group is employed, it is typically cleaved after affinity tagged peptides have been isolated using the affinity label together with the CR. In this case, any isotopic labeling in the linker preferably remains bound to the protein or peptide.

Linker groups include among others: ethers, polyethers, ether diamines, polyether diamines, diamines, amides, polyamides, polythioethers, disulfides, silyl ethers, alkyl or alkenyl chains (straight chain or branched and portions of which may be cyclic), aryl, diaryl or alkyl-aryl groups. Aryl groups in linkers can contain one or more heteroatoms (e.g., N, O or S atoms).

In one aspect, the invention provides a gel electrophoresis mass spectrometric method for identification and quantitation of one or more proteins in a complex mixture which employs affinity labeled reagents in which the PRG is a group that selectively reacts with certain amino acids or derivatives of amino acids that are typically found in proteins (e.g., sulfhydryl, amino, carboxy, homoserine lactone groups). Labeled reagents that optionally can contain an affinity label and with different PRG groups are introduced into a mixture containing proteins and the reagents react with certain proteins to tag them. In each case, it is necessary either to obtain stoichiometric protein modification with the isotope labeled reagent, or to modify the isotope labeled reagent so that the protein migrates homogeneously on the gel system to be employed. It may be necessary to pretreat the protein mixture to reduce disulfide bonds or otherwise facilitate labeling. After reaction with the labeled reagents, the multiple samples are combined, preferably in equal amounts, and the proteins in the complex mixture separated by either 1D or 2D gel electrophoresis. The gel is then stained to reveal the location of the proteins. The area of the gel containing the protein mixture or mixtures of interest is then excised and cleaved, e.g., enzymatically, into a number of peptides, or the gel is sliced uniformly so that all pieces can be analyzed. Alternatively, the proteins may be electroblotted to a membrane, and digestion performed on the membrane. As a third alternative, the proteins may be continuously eluted from the bottom of the gel and collected as fractions, followed by digestion. This digestion step may not be necessary, if the proteins are relatively small. After the peptides are purified, the protein(s) may be identified by means of peptide mass fingerprinting (PMF). When utilizing a reagent labeled with an affinity label, peptides that remain tagged with the affinity label are then isolated by an affinity isolation step, e.g., affinity chromatography, via their selective binding to the CR. Isolated peptides are released from the CR by displacement of A or cleavage of the linker, and released materials are analyzed by liquid chromatography/mass spectrometry (LC/MS). When a non-affinity labeled reagent is utilized, this affinity isolation step is not effected. The sequence of one or more tagged peptides is then determined by MSMS techniques, if necessary. In some cases, at least one peptide sequence derived from a protein will be characteristic of that protein and be indicative of its presence in the mixture. In other cases, the isotopically labeled peptide may be too short to uniquely identify a protein, and the use of PMF data may be necessary to identify the protein of origin. In other cases, the isotopically labeled peptides may be identical within a family of closely related proteins, which can then be distinguished by PMF or by MSMS analysis of other peptides present in the mixture that are unique to specific proteins. Finally, the high resolving power of 2D gel electrophoresis makes it possible to distinguish between different chemically modified forms of the same protein coding sequence, even if these proteins overlap in space with other unrelated proteins. Thus, the sequences of the peptides and the peptide mass fingerprint information together typically provide sufficient information to identify one or more proteins present in a mixture, even if the sequence of the isotopically labeled peptide is not sufficiently informative by itself.

The relative amounts of proteins in one or more different samples containing protein mixtures (e.g., biological fluids, cell or tissue lysates, etc.) can be determined using chemically identical but differentially isotopically labeled reagents. These reagents may, but need not, contain an affinity tag. In this method, each sample to be compared is treated with a different isotopically labeled reagent to label certain proteins therein. Tagged peptides originating from different samples are distinguished from one another by their mass, even though they have the same chemical composition. Peptides characteristic of their protein origin are identified using MS or $MS^n$ techniques allowing identification of proteins in the samples. The relative amounts of a given protein in each sample is determined by comparing relative abundance of the ions generated from any differentially labeled peptides originating from that protein. The method can be used to assess simultaneously the relative amounts of known proteins that originated in different samples. Further, since the method does not require any prior knowledge of the type of proteins that may be present in the samples, it can be used to identify proteins which are present at different levels in the samples examined. More specifically, the method can be applied to screen for and identify proteins which exhibit differential expression in cells, tissue or biological fluids. It is also possible to determine the absolute amounts of specific proteins in a complex mixture. In this case, a known amount of internal standard, one for each specific protein in the mixture to be quantified, is added to the sample to be analyzed. The internal standard is a peptide that is identical in chemical structure to the labeled peptide to be quantified except that the internal standard is differentially isotopically labeled than the peptide to be quantified. The internal standard can be provided in the sample to be analyzed in other ways. For example, a specific protein or set of proteins can be chemically tagged with an isotopically labeled reagent. A known amount of this material can be added to the sample to be analyzed. Also, it is possible to quantify the levels of specific proteins in multiple samples in a single analysis (multiplexing). In this case, affinity tagging reagents used to derivative proteins present in different labeled peptides from different samples can be selectively quantified by mass spectrometry.

The method of the present invention provides for quantitative measurement of specific proteins in biological fluids, cells or tissues and can be applied to determine global protein expression profiles in different cells and tissues. The same general strategy can be broadened to achieve the proteome-wide, qualitative and quantitative analysis of the state of modification of proteins, by employing labeled reagents with differing specificity for reaction with modified amino acid residues. The method of this invention can be used to identify low abundance proteins in complex mixtures and can be used to selectively analyze specific groups or classes of proteins such as membrane or cell surface proteins, or proteins contained within organelles, subcellular fractions, or biochemical fractions such as immunoprecipitates. Further, these methods can be applied to analyze differences in expressed proteins in different cell states. For example, the methods herein can be employed in diagnostic assays for the detection of the presence or the absence of one or more proteins indicative of a disease state, such as cancer.

DESCRIPTION OF THE SPECIFIC EMBODIMENTS

Figure 1:
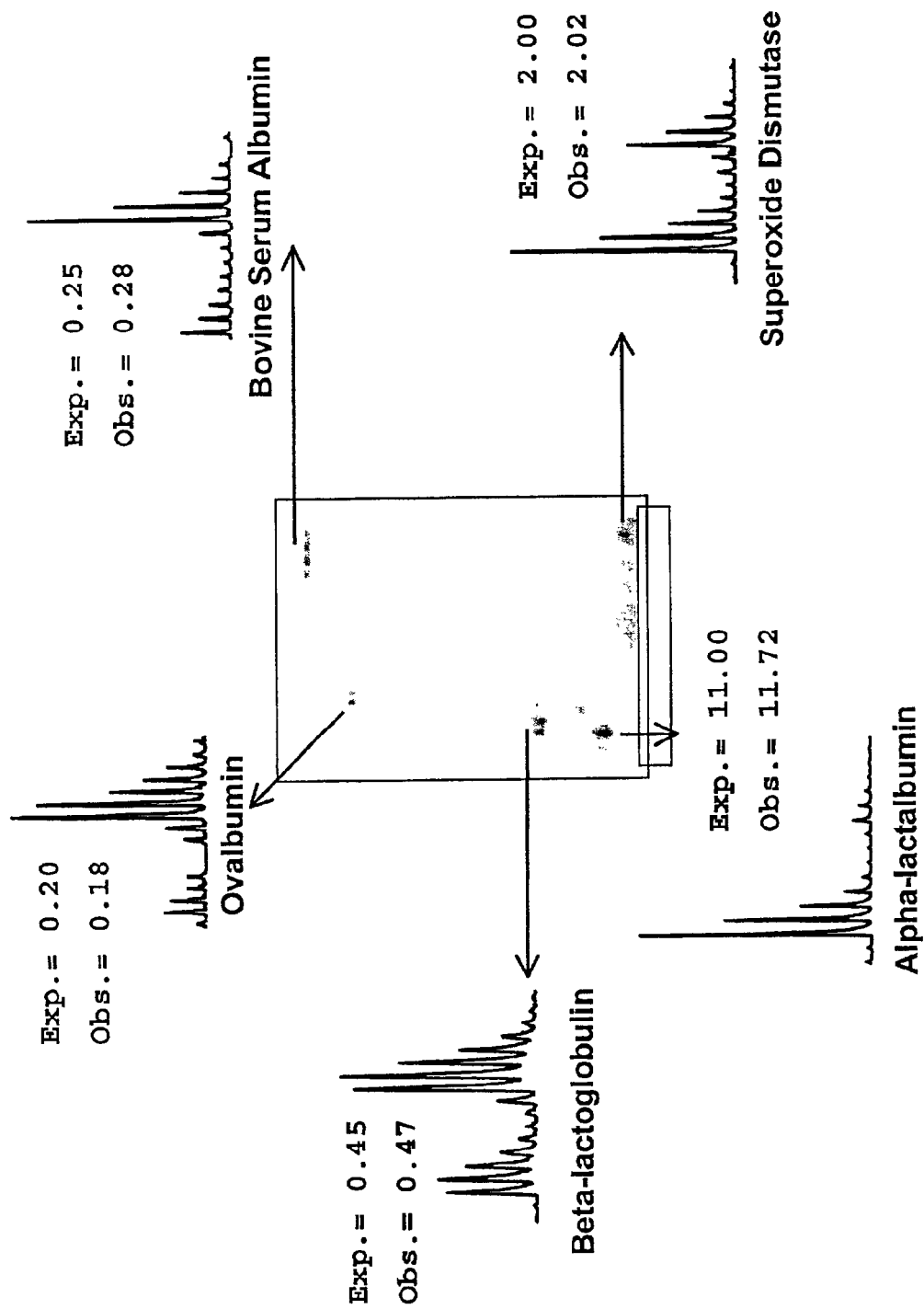
FIG. 1 is an image of a 2D gel onto which five different standard proteins had been loaded, with insets of mass spectra showing the regions that contained ICAT™ reagent pairs in accordance with the present invention. Also listed is the ratio at which the proteins were mixed prior to electrophoresis, and the ratio that was obtained upon measurement of the intensities of the ICAT reagent pairs.

One aspect of this invention employs affinity tagged protein reactive reagents in which the affinity tag is covalently attached to a protein reactive group by a linker or a reagent free of an affinity tag and which comprises a protein reactive group covalently attached to a linker. The linker is isotopically labeled to generate pairs or sets of reagents that are substantially chemically identical, but which are distinguishable by mass. For example a pair of reagents, one of which is isotopically heavy and the other of which is isotopically light can be employed for the comparison of two samples one of which may be a reference sample containing one or more known proteins in known amounts. For example, any one or more of the hydrogen, nitrogen, oxygen or sulfur atoms in the linker may be replaced with their isotopically stable isotopes $^2H$, $^{13}C$, $^{15}N$, $^{17}O$, $^{18}O$ or $^{34}S$.

When utilized, suitable affinity tags bind selectively either covalently or non-covalently and with high affinity to a capture reagent (CR). The CR-A interaction or bond should remain intact after extensive and multiple washings with a variety of solutions to remove non-specifically bound components. The affinity tag binds minimally or preferably not at all to components in the assay system, except CR, and does not significantly bind to surfaces of reaction vessels. Any non-specific interaction of the affinity tag with other components or surfaces should be disrupted by multiple washes that leave CR-A intact. Further, it must be possible to disrupt the interaction of A and CR to release peptides, substrates or reaction products, for example, by addition of a displacing ligand or by changing the temperature or solvent conditions. Preferably, neither CR nor A react chemically with other components in the assay system and both groups should be chemically stable over the time period of an assay or experiment. The affinity tag preferably does not undergo peptide-like fragmentation during (MS)" analysis. The affinity label is preferably soluble in the sample liquid to be analyzed and the CR should remain soluble in the sample liquid even though attached to an insoluble resin such as Agarose. In the case of CR, the term soluble means that CR is sufficiently hydrated or otherwise solvated such that it functions properly for binding to A. CR or CR-containing conjugates should not be present in the sample to be analyzed, except when added to capture A.

Examples of A and CR pairs include:

biotin or structurally modified biotin-based reagents, including iminobiotin, which bind to proteins of the avidin/streptavidin, which may, for example, be used in the forms of streptavidin-Agarose, oligomeric-avidin-Agarose, or monomeric-avidin Agarose;

any 1,2-diol, such as 1,2-dihydroxyethane (HO—$CH_2$—$CH_2$—OH), and other 1,2 dihyroxyalkanes including those of cyclic alkanes, e.g., 1,2-dihydroxycyclohexane which bind to an alkyl or aryl boronic acid or boronic acid esters, such as phenyl B(OH)$_2$ or hexyl-B(O Ethyl)$_2$ which may be attached via the alkyl or aryl group to a solid support material, such as Agarose;

maltose which binds to maltose binding protein (as well as any other sugar/sugar binding protein pair or more generally to any ligand/ligand binding protein pairs that has properties discussed above);

a hapten, such as dinitrophenyl group, for any antibody where the hapten binds to an anti-hapten antibody that recognizes the hapten, for example the dinitrophenyl group will bind to an anti-dinitrophenyl-IgG;

a ligand which binds to a transition metal, for example, an oligomeric histidine will bind to Ni(II), the transition metal CR may be used in the form of a resin bound chelated transition metal, such as nitrilotriacetic acid-chelated NI(ii) or iminodiacetic acid chelated Ni(II);

glutathione which binds to glutathione-S-transferase.

In general, any A-CR pair commonly used for affinity enrichment which meets the suitability criteria discussed above can be used. Biotin and biotin-based affinity tags are preferred. Of particular interest are structurally modified biotins, such as iminobiotin, which will elute from avidin or streptavidin columns under solvent conditions compatible with ESI-MS analysis, such as dilute acids containing 10–20% organic solvent. It is expected that iminobiotin tagged compounds will elute in solvents below pH 4. Iminobiotin tagged protein reactive reagents can be synthesized by methods described herein for the corresponding biotin tagged reagents. In one preferred embodiment, the affinity enrichment medium consists of monomeric avidin, which has a lower affinity for biotin than tetrameric avidin, and therefore can be recycled and used for the purification of peptides from many fractions.

A displacement ligand, DL, is optionally used to displace A from CR. Suitable DLs are not typically present in samples unless added. DL should be chemically and enzymatically stable in the sample to be analyzed and should not react with or bind to components (other than CR) in samples or bind non-specifically to reaction vessel walls. DL preferably does not undergo peptide-like fragmentation during MS analysis, and its presence in sample should not significantly suppress the ionization of tagged peptide, substrate or reaction product conjugates. DL itself preferably is minimally ionized during mass spectrometric analysis and the formation of ions composed of DL clusters is preferably minimal. The selection of DL, depends upon the A and CR groups that are employed. In general, DL is selected to displace A from CR in a reasonable time scale, at most within a week of its addition, but more preferably within a few minutes or up to an hour. The affinity of DL for CR should be comparable to or stronger than the affinity of the tagged compounds containing A for CR. Furthermore, DL should be soluble in the solvent used during the elution of tagged compounds containing A from CR. DL preferably is free A or a derivative or structural modification of A. Examples of DL include, biotin or biotin derivatives, particularly those containing groups that suppress cluster formation or suppress ionization in MS.

The linker group (L) should be soluble in the sample liquid to be analyzed and it should be stable with respect to chemical reaction, e.g., substantially chemically inert, with components of the sample as well as A and CR groups. The linker when bound to A should not interfere with the specific interaction of A with CR or interfere with the displacement of A from CR by a displacing ligand or by a change in temperature or solvent. The linker should bind minimally or preferably not at all to other components in the system, to reaction vessel surfaces or CR. Any non-specific interactions of the linker should be broken after multiple washes which leave the A-CR complex intact. Linkers preferably do not undergo peptide-like fragmentation during $(MS)^n$ analysis. At least some of the atoms in the linker groups should be readily replaceable with stable heavy-atom isotopes, The linker preferably contains groups or moieties that facilitate ionization of the affinity tagged reagents, peptides, substrates or reaction products.

To promote ionization, the linker may contain acidic or basic groups, e.g., COOH, $SO_3H$, primary, secondary or tertiary amino groups, nitrogen-heterocycles, ethers, or combinations of these groups. The linker may also contain groups having a permanent charge, e.g., phosphonium groups, quaternary ammonium groups, sulfonium groups, chelated metal ions, tetralkyl or tetraryl borate or stable carbanions.

The covalent bond of the linker to A or PRG should typically not be unintentionally cleaved by chemical or enzymatic reactions during the assay. In some cases it may be desirable to cleave the linker from the affinity tag A or from the PRG, for example to facilitate release from an affinity column. Thus, the linker can be cleavable, for example, by chemical, thermal, enzymatic or photochemical reaction. Photocleavable groups in the linker may include the 1-(2-nitrophenyl)-ethyl group. Thermally labile linkers may, for example, be a double-stranded duplex formed from two complementary strands of nucleic acid, a strand of a nucleic acid with a complementary strand of a peptide nucleic acid, or two complementary peptide nucleic acid strands which will dissociate upon heating. Cleavable linkers also include those having disulfide bonds, acid or base labile groups, including among others, diarylmethyl or trimethylarylmethyl groups, silyl ethers, carbamates, oxyesters, thioesters, thionoesters, and alpha-fluorinated amides and esters. Enzymatically cleavable linkers can contain, for example, protease-sensitive amides or esters, β-lactamase-sensitive β-lactam analogs and linkers that are nuclease-cleavable, or glycosidase-cleavable.

The protein reactive group (PRG) can be a group that selectively reacts with certain protein functional groups. Any selectively reactive protein reactive group should react with a functional group of interest that is present in at least a portion of the proteins in a sample. Reaction of PRG with functional groups on the protein should occur under conditions that do not lead to substantial degradation of the compounds in the sample to be analyzed. Examples of selectively reactive PRGs suitable for use in the affinity tagged reagents of this invention include those which react with sulfhydryl groups to tag proteins containing cysteine, those that react with amino groups, carboxylate groups, ester groups, phosphate reactive groups, and aldehyde and/or ketone reactive groups or, after fragmentation with CNBr, with homoserine lactone.

Thiol reactive groups include epoxides, alpha-haloacyl group, nitrites, sulfonated alkyl or aryl thiols and maleimides. Amino reactive groups tag amino groups in proteins and include sulfonyl halides, isocyanates, isothiocyanates, active esters, including tetrafluorophenyl esters, and N-hydroxysuccinimidyl esters, acid halides, and acid anhydrides. In addition, amino reactive groups include aldehydes or ketones in the presence or absence of $NaBH_4$ or $NaCNBH_3$.

Carboxylic acid reactive groups include amines or alcohols in the presence of a coupling agent such as dicyclohexylcarbodiimide, or 2,3,5,6-tetrafluorophenyl trifluoroacetate and in the presence or absence of a coupling catalyst such as 4-dimethylaminopyridine; and transition metal-diamine complexes including Cu(II) phenanthroline Ester reactive groups include amines which, for example, react with homoserine lactone.

Phosphate reactive groups include chelated metal where the metal is, for example Fe(III) or Ga(III), chelated to, for example, nitrilotriacetic acid or iminodiacetic acid.

Aldehyde or ketone reactive groups include amine plus $NaBH_4$ or $NaCNBH_3$, or these reagents after first treating a carbohydrate with periodate to generate an aldehyde or ketone.

The requirements discussed above for A, L, PRG, extend to the corresponding to the segments of A-L-PRG and the reaction products generated with this reagent.

Internal standards, which are appropriately isotopically labeled, may be employed in the methods of this invention to measure absolute quantitative amounts of proteins in samples. These may be prepared by reaction of affinity labeled protein reactive reagents with a preparation known to contain the protein of interest to generate the affinity tagged peptides generated from digestion of the tagged protein. Alternatively, the desired peptides may be chemically synthesized. Affinity tagged peptide internal standards are substantially chemically identical to the corresponding affinity tagged peptides generated from digestion of the affinity tagged protein, except that they are differentially isotopically labeled to allow their independent detection by MS techniques.

The method of this invention can also be applied to determine the relative quantities of one or more proteins in two or more protein samples, while simultaneously determining their identity. The proteins in each sample are reacted with the labeled reagents which are substantially chemically identical but differentially isotopically labeled. The samples are combined and processed as one, and then run together by gel electrophoresis. The proteins contained in specific bands or spots are then digested. Alternatively, after mixing the protein samples, but prior to electrophoresis, the proteins may be subjected to avidin affinity chromatography to enrich for biotinylated proteins, which could be important, for example, if intact cells had been labeled. The relative quantity of each labeled peptide, which reflects the relative quantity of the protein from which the peptide originates, is determined by the measurement of the respective isotope peaks by mass spectrometry.

The methods of this invention can be applied to the analysis or comparison of multiple different samples. Samples that can be analyzed by methods of this invention include cell homogenates; cell fractions; biological fluids including urine, blood, and cerebrospinal fluid; tissue homogenates; tears; feces; saliva; lavage fluids such as lung or peritoneal lavages; mixtures of biological molecules including proteins, lipids, carbohydrates and nucleic acids generated by partial or complete fractionation of cell or tissue homogenates.

The methods of this invention employ MS and $(MS)^n$ methods. While a variety of MS and $(MS)^n$ are available and may be used in these methods, Matrix Assisted Laser Desorption Ionization MS (MALDI/MS) and Electrospray Ionization MS (ESI/MS) methods are preferred.

As set forth above, the proteins in each sample are labeled with either an (A) affinity labeled or a non-affinity labeled reagent both of which include a labeled linker moiety (L) and a protein reactive group (PRG).

The labeled samples are mixed and then preferably subjected to 2D PAGE. One dimensional SDS electrophoresis can be used instead of 2D PAGE, or one dimensional isoelectric focusing gels, or any other electrophoretic method for separating proteins, including native protein electrophoresis. The procedures for running one dimensional and two dimensional electrophoresis are well known to those skilled in the art.

Proteins that the two cell samples have in common form coincident spots upon protein staining, or upon direct MS analysis of a piece of the gel. The ratio of the detectable isotopes between identical proteins from either sample will be constant for the vast majority of proteins. Proteins that the two samples do not have in common will migrate independently. Thus, a protein that is unique or of different relative concentration to one sample will have a different ratio of detectable isotopes from the majority of protein spots. The protein spots of interest then are digested to form labeled peptides which then are analyzed by $(MS)^n$.

In conventional analysis, a control is run with known proteins for the cell type being studied. The known spots on the sample gel have to be identified and marked, then compared to the control and the second gel to determine differences between the two gels. In the present invention, there is only one gel so no marking is necessary. In addition, the software used on conventional processes for alignment of different gels prior to comparing and contrasting protein differences does not correct for local distortions and inconsistencies between two or more gels. The process of the present invention eliminates the need for such correction because the extracts for all samples to be tested are mixed and run on the same gel. Any gel distortions are experienced equally by each sample.

One of the advantages of performing gel electrophoresis is that proteins of particular interest migrate to a reproducible place on the gel, so that if desired, only these proteins need be analyzed. These proteins can include disease markers as well as control proteins. Many of the post-translationally modified forms of these proteins can be separated from one another by gel electrophoresis, so that the methods of the invention could be used to determine and quantify changes in the expression of each of these modified forms. If there was any difficulty in localizing such proteins, a small portion of the separated samples could be transblotted from the gel and these proteins could be located by immunoblotting techniques. Alternatively, a small amount of the protein of interest could be labeled with a fluorescent marker known not to affect migration position prior to electrophoresis to identify the regions of interest to be analyzed. Then the methods of this invention could be used to measure the quantitative changes in the majority of the proteins in the gel based upon the PRG as a function of their migration on the gel.

The method of this invention can be utilized to analyze the protein composition described in Published PCT application WO 00/11208 which is incorporated herein by reference.

Quantitative Proteome Analysis with Affinity Labeled Reagent

This method consists of using a biotin labeled sulfhydryl-reactive reagent for quantitative protein profile measurements in a sample protein mixture and a reference protein mixture. The method comprises the following steps:

A. Reduction Disulfide bonds of proteins in the sample and reference mixtures are reduced to free SH groups. The preferred reducing agent is tri-n-butylphosphine which is used under standard conditions. Alternative reducing agents include tricarboxyethylphosphine, mercaptoethylamine and dithiothreitol. If required, this reaction can be performed in the presence of solubilizing agents including high concentrations of urea and detergents to maintain protein solubility. The reference and sample protein mixtures to be compared are processed separately, applying identical reaction conditions.

B. Derivatization of SH groups with an affinity tag Free SH groups are derivatized with the biotinylating reagent biotinyl-iodoacetylamidyl-4,7, dioxadecanediamine. The reagent is prepared in different isotopically labeled forms by substitution of linker atoms with stable isotopes and each sample is derivatized with a different isotopically labeled form of the reagent. Derivatization of SH groups is preferably performed under slightly basic conditions (pH 8.5) for 90 minutes at room temperature. For the quantitative, comparative analysis of two samples, one sample each (termed reference sample and sample) are derivatized with the isotopically light and the isotopically heavy form of the reagent, respectively. For the comparative analysis of several samples one sample is designated a reference to which the other samples are related to. Typically, the reference sample is labeled with the isotopically heavy reagent and the experimental samples are labeled with the isotopically light form of the reagent, although this choice of reagents is arbitrary. These reactions are also compatible with the presence of high concentrations of solubilizing agents.

C. Combination of labeled samples After completion of the affinity tagging reaction defined aliquots of the samples labeled with the isotopically different reagents (e.g., heavy and light reagents) are combined and all the subsequent steps are performed on the pooled samples. Combination of the differentially labeled samples at this early stage of the procedure eliminates variability due to subsequent reactions and manipulations. Preferably equal amounts of each sample are combined; and then fractionated by one of the following well known techniques:

1.) Flow Through Gel electrophoresis The labeled proteins are separated through a preparative flow-through SDS gel (5%) apparatus (Mini Prep Cell, Bio-Rad) and the eluted proteins are collected in fractions. The proteins may be concentrated, for example, by acetone precipitation before proteolytic digestion is effected by overnight incubation with an enzyme such as trypsin.

2.) Standard gel electrophoresis The gel may be stained for proteins to localize spots or bands, or the spots or slices may be processed without protein detection at this stage. Protein mixtures that are present in a spot (2D) or band (1D) by gel electrophoresis are excised from the gel, optionally dried and digested with an enzyme. The proteins in the sample mixture are digested, typically with trypsin. Alternative proteases are also compatible with the procedure as in fact are chemical fragmentation procedures. This step may be omitted in the analysis of small proteins.

3.) Standard gel electrophoresis with digestion and transblotting for peptide extraction The gel may be treated with enzymes and transblotted (with or without the aid of electric current) onto a membrane, or transblotted through an active protease membrane and captured on a second membrane (Bienvenut et al., Anal. Chem. 71:4800–4807, 1999). That membrane can then be directly analyzed by MS or MALDI MSMS.

D. Peptide Mass Fingerprinting The protein digest may then be submitted to PMF to identify the major protein components. In favorable instances, the Cys-containing biotinylated peptides are detectable at this stage as isotope pairs that are 8 amu apart, and the relative amount of the proteins can be determined by comparing the intensities of these peptides in the mass spectrum without additional purification.

E. Affinity isolation of the affinity tagged peptides by interaction with a capture reagent The biotinylated peptides may then be isolated on avidin-agarose. After digestion the pH of the peptide samples is lowered to 6.5 and the biotinylated peptides are immobilized on beads coated with monomeric avidin (Promega). The beads are extensively washed. The last washing solvent includes 10% acetonitrile to remove residual SDS. Biotinylated peptides are eluted from avidin-agarose, for example, with 0.4% trifluoroacetic in the presence of acetonitrile.

Analysis of the isolated, derivatized peptides may also be accomplished by μLC-MS$^n$ or CE-MS$^n$ with data dependent fragmentation. Methods and instrument control protocols well-known in the art and described, for example, in Ducret et al., 1998; Prot.Sci. 7: 706–719, Figeys and Aebersold, 1998 Electrophoresis 19: 885–892; Figeys et al., 1996, Nature Biotech. 14:1579–1583; or Haynes et al., 1998 Electrophoresis 19:939–945 are used and which are incorporated herein by reference. In this last step, both the quantity and sequence identity of the proteins from which the tagged peptides originated can be determined by automated multistage MS. This is achieved by the operation of the mass spectrometer in a dual mode in which the instrument alternates in successive scans between measuring the relative quantities of peptides eluting from the capillary column and recording the sequence information of selected peptides. Peptides are quantified by measuring in the MS mode the relative signal intensities for pairs of peptide ions of identical sequence that are tagged with the isotopically light or heavy forms of the reagent, respectively, and which, therefore, differ in mass by the mass differential encoded within the affinity tagged reagent. Peptide sequence information is automatically generated by selecting peptide ions of a particular mass-to-charge (m/z) ratio for collision-induced dissociation (CID) in the mass spectrometer operating in the MS$^n$ mode. See Link, A. J. et al. Electrophoresis 18:1314–1334, 1997; Gygi, S. P. et al. Mol.Cell. Biol. 19:1720–1730, 1999, and Gygi, S. P. et al. Electrophoresis 20:310–319, 1999 and which are incorporated herein by reference. The resulting CID spectra are then automatically correlated with sequence databases to identify the protein from which the sequenced peptide originated. The combination of the results generated by MS and MSMS analyses of affinity tagged and differentially labeled peptide samples determines the relative quantities as well as the sequence identities of the components of protein mixtures in a single, automated operation.

This method can also be practiced using other affinity tags and other protein reactive groups, including amino reactive groups, carboxyl reactive groups, or groups that react with homoserine lactones.

The approach employed herein for quantitative proteome analysis is based on two principles. First, a short sequence of contiguous amino acids from a protein (5–25 residues) contains sufficient information to uniquely identify that protein. Protein identification by MS$^n$ is accomplished by correlating the sequence information contained in the CID mass spectrum with sequence databases, using sophisticated computer searching algorithms (Eng, J. et al. J. Amer. Soc. Mass Spectrom. 5: 976–989, 1994; Mann, M. et al. Anal Chem. 66: 4390–4399, 1994; Qin, J. et al. Amer. Chem. 69: 3995–4001, 1997; Clauser, K. R. et al. Proc. Nat. Acad. Sci. USA 92:5072–5076, 1995 which are incorporated herein by reference). Second, pairs of identical peptides tagged with the light and heavy affinity tagged reagents, respectively, (or in analysis of more than two samples, sets of identical tagged peptides in which each set member is differentially isotopically labeled) are chemically identical and therefore serve as mutual internal standards for accurate quantitation. The MS measurement readily differentiates between peptides originating from different samples, representing for example different cell states, because of the difference between isotopically distinct reagents attached to the peptides. The ratios between the intensities of the differing weight components of these pairs or sets of peaks provide an accurate measure of the relative abundance of the peptides (and hence the proteins) in the original cell pools because the MS intensity response to a given peptide is independent of the isotopic composition of the reagents (De Leenheer, A. P. et al, Mass. Spectrom. Rev. 11:249–702, 1992) which are incorporated herein by reference. The use of isotopically labeled internal standards is standard practice in quantitative mass spectrometry and has been exploited to great advantage in, for example, the precise quantitation of drugs and metabolites in bodily fluids.

The methods of this invention, in particular 1D gels, can be applied to analysis of classes of proteins with particular physical-chemical properties including poor solubility, large or small size and extreme pI values. Low abundance proteins can be analyzed by performing protein affinity subtraction prior to electrophoresis to remove the most abundant proteins. Alternatively, the biotinylation reaction could be performed in such a way as to label a minor subset of proteins, for example, those proteins exposed on the ouside of a cell, or proteins that remain exposed after organelle purification. Because a large amount of non-biotinylated protein would then be present that would otherwise interfere with electrophoresis, after mixing the proteins from the control and experimental together, the protein preparation could be subjected to avidin affinity chromatography to enrich for the biotinylated proteins, which would then be electrophoresed.

The prototypical application of the chemistry and method of the present invention is the establishment of quantitative profiles of complex protein samples and ultimately total lysates of cells and tissues following the preferred method described above. In addition the reagents and methods of this invention have applications which go beyond the determination of protein expression profiles. Such applications include the following:

The application of amino-reactive or sulfhydryl-reactive, differentially isotopically labeled affinity tagged reagents can be used for the quantitative analysis of proteins in immunoprecipitated complexes. In the preferred version of this technique protein complexes from cells representing different states (e.g., different states of activation, different disease states, different states of differentiation) are precipitated with a specific reagent, preferably an antibody. The proteins in the precipitated complex are then derivatized and analyzed as above.

The application of amino-reactive, differentially isotopically labeled affinity tagged reagents can be used to determine the sites of induced protein phosphorylation. In a preferred version of this method purified proteins (e.g., immunoprecipitated from cells under different stimulatory conditions) are fragmented and derivatized as described above. Phosphopeptides are identified in the resulting peptide mixture by fragmentation in the ion source of the ESI-MS instrument and their relative abundances are determined by comparing the ion signal intensities of the experimental sample with the intensity of an included, isotopically labeled standard.

Amino-reactive, differentially isotopically labeled affinity tagged reagents are used to identify the N-terminal ion series in MSMS spectra. In a preferred version of this application, the peptides to be analyzed are derivatized with a 50:50 mixture of an isotopically light and heavy reagent which is specific for amino groups. Fragmentation of the peptides by CID therefore produce two N-terminal ion series which differ in mass precisely by the mass differential of the reagent species used. This application dramatically reduces the difficulty in determining the amino acid sequence of the derivatized peptide.

The following examples illustrate four different experiments in which gel electrophoresis separations were performed and quantitative data were obtained using ICAT™ reagents that contained a biotinyl affinity tag, a linker with eight deuterium atoms, and an iodoacetamide protein reactive group. These examples are not exhaustive and are not intended to limit the scope of these experiments.

EXAMPLES

Example 1

Five different standard proteins were alkylated separately with the d0 ICAT reagent and the d8 ICAT reagent, and mixed together in different ratios prior to performing 2D gel electrophoresis. After staining, the spots corresponding to these proteins were cut out, digested with trypsin, and submitted to PMF. FIG. 1 shows an image of the gel and insets of each mass spectrum that contain one of the ICAT reagent pairs from each protein. In addition, the ratio at which the proteins were mixed together prior to gel electrophoresis is listed, as well as the ratio of d0 to d8 that was obtained by mass spectrometry. In all five cases, the discrepancy between the experimental and the observed ratios was well below 20%.

Figure 2:
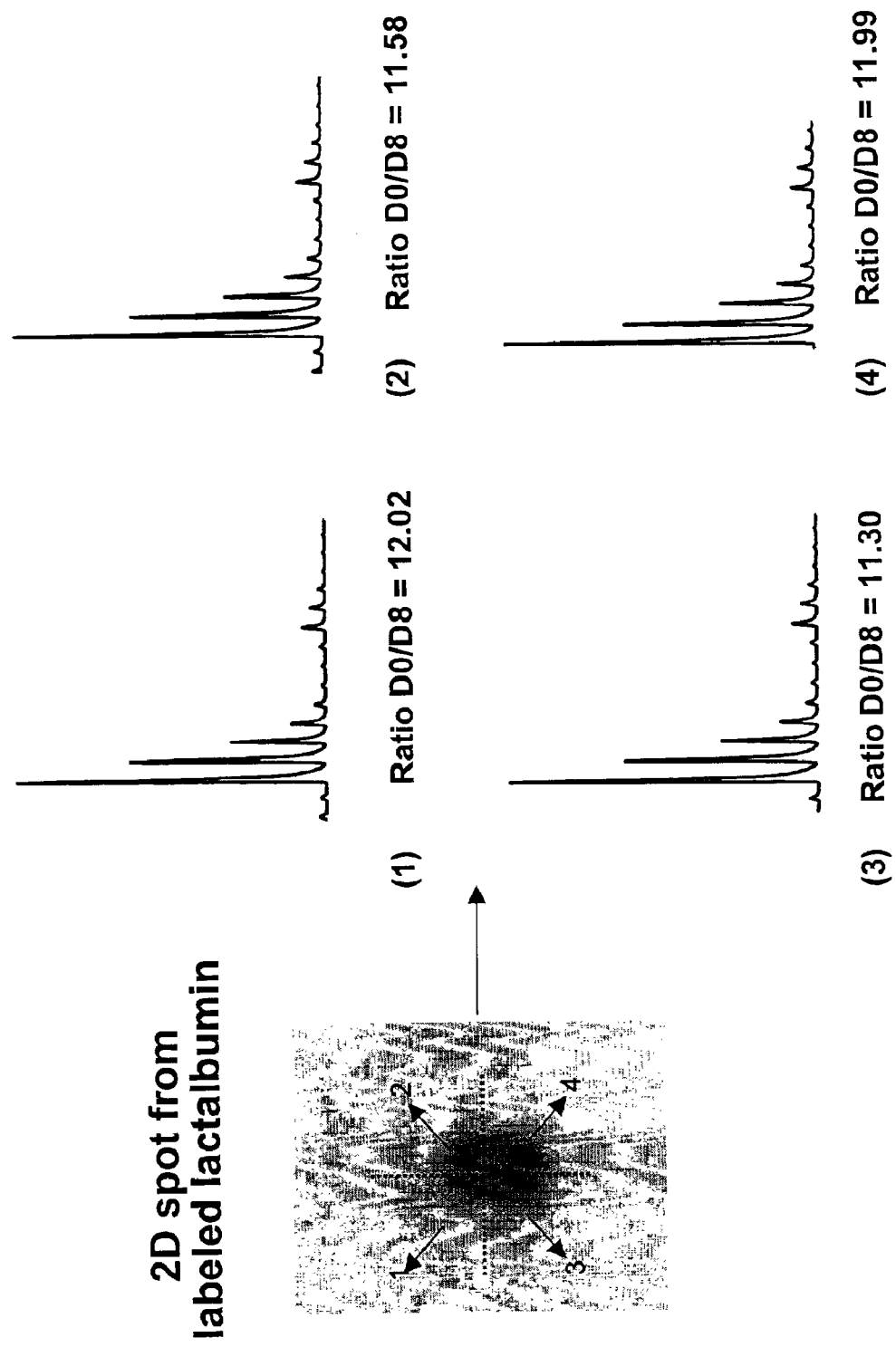
FIG. 2 is an expanded view of the spot for lactalbumin, segmented into quadrants. Also shown are the regions of a mass spectrum containing one ICAT reagent pair, and the intensity ratio that was determined for each of them in accordance with the present invention.

One of the problematic aspects of separating ICAT reagent labeled peptides by HPLC is that the d8 labeled peptide typically elutes several seconds ahead of the corresponding d0 labeled peptide. To demonstrate the fact that upon gel electrophoresis there is no similar isotope separation effect, the 2D spot for lactalbumin, shown in FIG. 2, was split into quadrants, which were then separately digested, extracted, and submitted to MALDI MS analysis. The right hand side of FIG. 2 demonstrates that the same ratio of d0 to d8 was obtained for each of these quadrants, within 10%.

Example 2

*E. coli* bacteria lysates, either labeled with an ICAT reagent comprising deuterated biotinyl iodoacetamide reagent for minimum medium (glucose) growing condition or labeled with non-deuterated reagent for rich medium (LB broth) growing condition, were mixed at equal amounts. The mixture was separated through a preparative flow-through SDS gel (5%) apparatus (Mini Prep Cell, Bio-Rad) and proteins were fractionated into solution. The fractionated proteins were then acetone precipitated before proteolytic digestion by overnight incubation with trypsin. Upon avidin chromatography, peptides from both the flow-through portion and the elution portion were collected into 96 fractions. The flow-through was captured on reversed phase medium (POROS® 50R1, Applied Biosystems) and washed with distilled water and eluted with 60% ACN. Samples were vacuum dried and re-suspended with 50% ACN/0.1% TFA. Spectra were acquired using an Applied Biosystems Voyager MALDI TOF mass spectrometer with α-cyano-4-hydroxycinnamic acid as matrix. The strategy was to identify proteins using PMF, while the d0/d8 ratio was used for quantitation.

Figure 3:
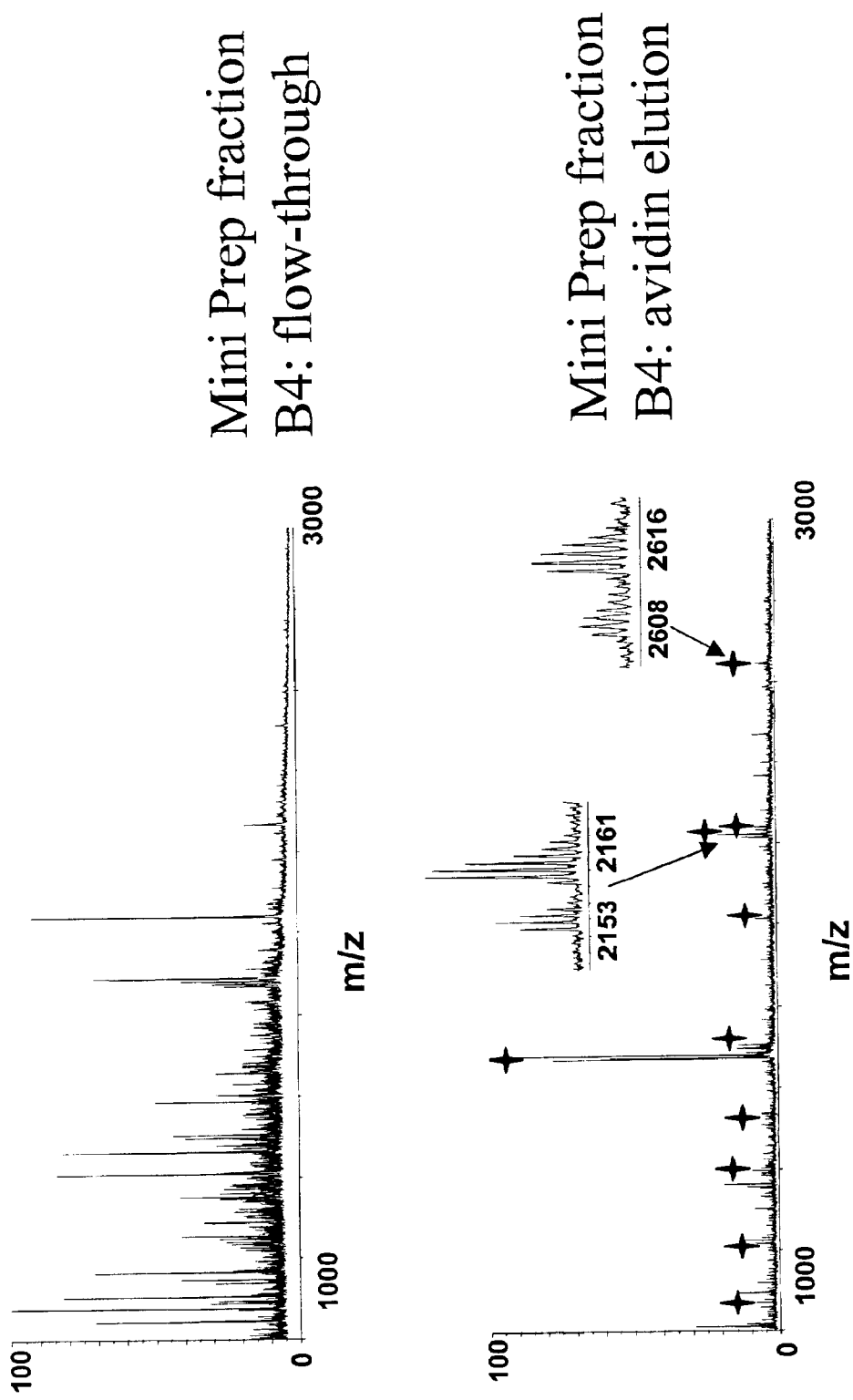
FIG. 3 is a set of mass spectra obtained from one fraction of a mixture of two lysates of E. coli that had been labeled separately with ICAT reagent prior to electrophoresis through a flow-through gel apparatus in accordance with the present invention. The first panel shows the entire peptide mass fingerprint that was obtained for one particular fraction after digestion with trypsin, and the second panel shows the peptides that were retained and eluted from avidin beads for this fraction. Two ICAT reagent pairs are shown in the insets.

FIG. 3 shows the spectrum acquired for the avidin flow through and for the peptides eluted from the avidin for one fraction that contained proteins at about 40,000 in molecular weight. Ten (10) different ICAT reagent labeled pairs are marked. The major protein components were tentatively identified by PMF using the ChemApplex PMF software program (Applied Biosystems), and six components are listed in Table 1 below. OmpA was the main component, which comprised 25% of the total intensity. The confidence in the identification is roughly proportional to the score listed in column 5. Note that all six of these proteins have molecular weights that are between 30K and 52K daltons, as would be expected using crude SDS separation. A special peptide database was created containing cysteine peptides only, and the masses from the eluted peptides were searched against this database. The top six candidate proteins are listed. Two of these proteins are identical to those identified from the avidin flow through. Notably, two of the proteins in the flow through fraction, namely, ribose binding protein and outer membrane C, have no cysteines, and therefore would not contribute any peptides to the avidin eluate fraction.

TABLE I

| Acc. # | Protein Name | MW | # peptide | Score | % Intensity | ppm | ratio |
|---|---|---|---|---|---|---|---|
| | | | Flow-Through | | | | |
| P02990 | EF-TU | 43156 | 6 | 47828 | 25.4 | 3.7 | |
| P06996 | ompC | 40344 | 8 | 13194 | 12.7 | 7.3 | |
| P00477 | SHT | 45289 | 4 | 7778 | 5.1 | 4.2 | |
| P02925 | ribose BP | 30932 | 5 | 4488 | 7.4 | 10.7 | |
| P06711 | glutamine syn. | 51741 | 4 | 4196 | 3.4 | 7.7 | |
| P08200 | ICDH | 45728 | 3 | 1174 | 1.6 | 6.6 | |
| | | | Avidin Elution | | | | |
| P02990 | EF-TU | 43156 | 5 | 17822 | 48.2 | 3.2 | 0.65 |
| P02934 | ompA | 37179 | 2 | 305 | 2.2 | 3.3 | 0.67 |
| P39342 | hypo. 54.3 | 54299 | 2 | 91 | 0.6 | 10.3 | 0.49 |
| P76200 | hypo. 43 | 41368 | 2 | 44 | 1.7 | 18.4 | 2.6 |
| P07460 | succ.coA syn. | 41368 | 2 | 21 | 1.1 | 14.2 | 1.5 |
| P00477 | SHT | 45289 | 3 | 1 | 0.2 | 28.3 | 0.13 |

The proteins listed in Table I were identified from the spectra in FIG. 3 using the ChemApplex PMF program. The top panel was obtained from the flow-through of the avidin beads, and the bottom panel was obtained from the avidin elution. The first column lists the SwissProt accession number of the protein that was identified. The second column lists an abbreviated form of the protein's name: EF-TU for elongation factor-TU, ompC for outer membrane protein C, SHT for serine hydroxymethyl transferase, ribose BP for the periplasmic ribose binding protein, glutamine syn. for glutamine synthetase, ICDH for isocitrate dehydrogenase, ompA for outer membrane protein A, hypo. for hypothetical protein, succ. CoA syn. for succinyl coenzyme A synthetase beta chain. The MW column lists the molecular weight of the protein; # peptide lists the number of peptides that were matched (including only the d0 masses for the avidin eluted peptides); the Score was calculated by the ChemApplex program taking into account only the d0 masses; % Intensity is the percentage of the intensity of all the masses in the spectrum that could be accounted for by the masses that were matched (again only the d0 masses); and ppm is the average intensity-weighted ppm error for those masses between the experimental measurements from the mass spectrum and the theoretical mass of the peptides. Ratio was calculated manually by dividing the intensity of the d0 peptide by the intensity for the corresponding d8 peptide, and averaging where possible. The low intensity of the d0 masses for SHT explains why the ChemApplex program had difficulty in distinguishing SHT from the noise; the program was not looking for the d8 masses, all three of which are detectable over the background. Note that ompC and RBP do not contain cysteines, and therefore are invisible in the avidin eluate fraction. The confidence in the identifications is highest for the proteins with the highest score, and also for the proteins that were independently identified in the flow-through fraction and the affinity elution sample. All of the proteins in both tables except the two hypothetical proteins in the second table have been identified repeatedly from these *E. coli* lysates.

Example 3

Two *E coli* preparations similar to those described above were labeled with ICAT d0 reagent and ICAT d8 reagent, mixed together and submitted to 1D SDS gel analysis. Slices were cut from the gel, washed, digested with trypsin, and the peptides were eluted. No avidin affinity chromatography was performed, so that only the most intense ICAT reagent labeled peptides were detectable. Upon PMF analysis with ChemApplex, *E. coli* tryptophanase was detectable as the most prominent protein component, after trypsin itself. Under these conditions, the peptides that corresponded to ICAT reagent pairs were also detected in an oxidized form, due to oxidation at the original cysteine sulfur atom, analogous to the oxidation of methionine residues that is commonly observed post SDS gel analysis. Thus, each peptide provides two independent measurements of the ratio of d0 to d8, one for the reduced form of the peptide, and one for the oxidized form of the peptide. A prominent quartet of peaks about 8 amu apart was detected starting at 1581.85, which corresponds to the tryptophanase peptide QLPCPAELLR (SEQ ID NO: 1), and the d8, d0+O and d8+O peaks. The ICAT reagent pair with an unmodified methionine had a d8/d0 ratio of 2.1, whereas the oxidized pair had a d8/d0 ratio of 1.9. In these experiments, the ratios obtained for ICAT reagent pairs of peptides derived from the same protein were commonly within 20% of each other, except for the weakest signals and those signals that obviously overlapped other peptides (which is particularly apparent when they correspond to expected trypsin digestion products from the same proteins already identified). Other ICAT reagent pairs from tryptophanase were detectable, but not well resolved over the background.

Example 4

Proteins were isolated from rat cardiac cells from normal myocytes or from myocytes that had been subjected to ischemic conditions. Normal rat proteins were labeled with the d0 ICAT reagent, and the ischemic cell proteins were labeled with the d8 ICAT reagent. The two samples were mixed together, and run on a 2D gel, and stained with Coomassie brilliant blue. Spots were cut out, digested with trypsin, and submitted to PMF. The data were then searched using the ChemApplex software program, using a database that consisted of all of the human, rat and mouse proteins in the SwissProt database. The top candidate for one spot was human citrate synthetase. The rat and mouse homologues of citrate synthetase were absent from the database. The peptide mass fingerprint spectrum contained a prominent ICAT reagent pair at 1098 that did not correspond to any of the citrate synthetase peptides. Because the rat citrate synthetase protein was not present in the SwissProt database, a rat EST database was searched in the Protein Prospector (University of California-San Francisco) software program using masses that corresponded exactly to the theoretical masses of citrate synthetase that had been identified. One of the EST sequences that was identified by this means contained the sequence YSQCR (SEQ ID NO: 2), which corresponded to the ICAT reagent pair at 1098. The homologous human sequence was YTQCR (SEQ ID NO: 3), explaining the measured mass did not match the sequence in the database. This peptide sequence is too short to be a unique identifier of a protein, and would not be useful had it not been possible to assign the peptide to citrate synthetase on the basis of the PMF data.

We claim:

1. A method of comparing protein compositions of interest between at least two different samples which comprises:
   (a) preparing an extract of proteins from each of said at least two different samples;
   (b) providing a set of substantially chemically identical and differentially isotopically labeled protein reagents, wherein said reagent has a formula selected from the group consisting of:

A-L-PRG and L-PRG, wherein A is an affinity label that selectively binds to a captive reagent, L is a linker group in which one or more atoms are differentially labeled with one or more stable isotopes and PRG is a protein reactive group that selectively reacts with a given protein functional group or is a substrate for an enzyme;
   (c) reacting the extract proteins from different samples of step (a) with a different isotopically labeled reagent from said set of step (b) to provide two or more sets of isotopically differentially labeled proteins;
   (d) mixing each of said two or more sets of isotopically differentially labeled proteins to form a single mixture of isotopically differentially labeled proteins;
   (e) separating two or more differentially labeled proteins in the mixture of step (d) by electrophoresing said mixture;
   (f) digesting at least a portion of the proteins that have been subjected to electrophoresis in step (e) to produce a sample of labeled peptides; and
   (g) detecting the difference in the expression levels of one or more differentially labeled proteins in the at least two different samples by mass spectrometry based on one or more differentially labeled peptides in the sample of labeled peptides.

2. The method of claim 1 wherein said reagent has the formula:

A-L-PRG and affinity tagged proteins in the samples are enzymatically or chemically processed to convert them into labeled peptides.

3. The method of claim 1 wherein said reagent has the formula:

L-PRG and labeled proteins in the samples are enzymatically or chemically processed to convert them into labeled peptides.

4. The method of any one of claims 1, 2 or 3 wherein the protein or peptide portion of one or more of the labeled proteins are sequenced by tandem mass spectrometry to identify the labeled protein from which the peptide originated.

5. The method of any one of claims 1, 2 or 3 wherein the proteins are identified by peptide mass fingerprinting, and the isotopically labeled peptides are used for quantitation.

6. The method of any one of claims 1, 2 or 3 in which the amount of one or more proteins or peptides in the samples is also determined by mass spectrometry and which further comprises the step of introducing into a sample a known amount of one or more internal standards for each of the proteins to be quantified.

7. The method of any one of claims 1, 2 or 3 wherein the released isotopically labeled proteins or peptides are separated by chromatography prior to detecting and detection by mass spectrometry.

8. The method of claims 1, 2 or 3 where the samples consist of protein mixtures derived from the group consisting of: tissues, cells, serum, cerebrospinal fluid, urine, ascites, subcellular fractions, supernatants, membrane-containing organelles, nuclear preparations, and protein preparations separated by chromatographic methods, capillary electrochromatography or capillary electrophoresis methods.

9. The method of claims 1, 2 or 3 where the proteins are identified by any protein staining technique, or where protein-containing regions are localized by mass spectrometry following systematic digestion and extraction or any combination of transblotting and digestion.

10. The method of any one of claims 1, 2 or 3 in which a plurality of proteins or peptides in one sample are detected and identified.

11. The method of any one of claims 1, 2 or 3 further comprising a step in which one or more of the proteins or peptides in a sample are chemically or enzymatically processed to expose a functional group that can react with a label.

12. The method of any one of claims 1, 2 or 3 wherein PRG is a protein reactive group that selectively reacts with certain protein functional groups and a plurality of proteins or peptides are detects and identified in a single sample.

13. The method of claim 12 wherein two or more substantially chemically identical and differentially isotopically labeled protein reactive reagents having different specificities for reaction with proteins or peptides are provided and reacted with each sample to be analyzed.

14. The method of claim 13 wherein all of the proteins or peptides in a sample are detected and identified.

15. The method of any one of claims 1, 2 or 3 wherein the relative amounts of one or more proteins or peptide in two or more different samples are determined and which further comprises the steps of combining the differentially labeled samples, capturing isotopically labeled components from the combined samples and measuring the relative abundances of the differentially labeled proteins or peptides.

16. The method of any one of claims 1, 2 or 3 wherein step (g) comprises determining the relative amounts of membrane proteins in one or more different samples.

17. The method of claim 15 in which different samples contain proteins originating from different organelles or different subcellular fractions.

18. The method of claim 15 in which different samples represent proteins or peptides expressed in response to one or more different environmental conditions, different nutritional conditions, different chemical stimuli, different physical stimuli, and at different times.

19. The method of claim 1 wherein absolute protein concentration is deduced by comparison to a known amount of a deuterated or non-deuterated peptide standard, where this standard was derived by chemical synthesis or was isolated from biological samples.

20. The method of claim 1 whereby multiple samples are labeled with PRG containing different numbers of heavy atoms so that multiple samples can be separated on a single gel and analyzed at one time.

21. The method of claim 1 whereby proteins of interest are analyzed based on their location within one or more of of a 1D gel, a 2D gel, or a combination thereof.

22. The method of claim 1 whereby the post-translational modification status of particular proteins are monitored by gel analysis.

* * * * *